US008301466B2

(12) United States Patent
Lorsch

(10) Patent No.: US 8,301,466 B2
(45) Date of Patent: *Oct. 30, 2012

(54) METHOD AND SYSTEM FOR PROVIDING ONLINE RECORDS

(75) Inventor: Robert H. Lorsch, Los Angeles, CA (US)

(73) Assignee: Mymedicalrecords, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,809

(22) Filed: Mar. 7, 2011

(65) Prior Publication Data

US 2011/0154508 A1    Jun. 23, 2011

Related U.S. Application Data

(63) Continuation of application No. 12/204,498, filed on Sep. 4, 2008, which is a continuation of application No. 11/305,685, filed on Dec. 16, 2005, now Pat. No. 8,117,045, which is a continuation-in-part of application No. 11/225,518, filed on Sep. 12, 2005, now Pat. No. 8,121,855.

(51) Int. Cl.
*G06Q 100/00* (2006.01)
*G06Q 50/00* (2006.01)
*A61B 5/00* (2006.01)
*G06F 19/00* (2006.01)

(52) U.S. Cl. ............................................. 705/3; 705/2

(58) Field of Classification Search ................... 705/2–3
See application file for complete search history.

(56) References Cited

U.S. PATENT DOCUMENTS

| 5,404,292 A | 4/1995 | Hendrickson |
| 5,494,292 A | 2/1996 | Mileti |
| 5,499,293 A | 3/1996 | Behram et al. |
| 5,778,882 A | 7/1998 | Raymond et al. |

(Continued)

FOREIGN PATENT DOCUMENTS

EP    0764911 A1    3/1997

(Continued)

OTHER PUBLICATIONS

MyMedicalRecords.com, Inc., Examiner's Report from Australian Patent Application No. 2006202057, dated Jul. 31, 2007, 2 pages.

(Continued)

*Primary Examiner* — Robert Morgan
*Assistant Examiner* — Joy Chng
(74) *Attorney, Agent, or Firm* — McKee, Voorhees & Sease, P.L.C.

(57) ABSTRACT

A method for providing a user with the ability to access and collect records associated with the user in a secure and private manner includes associating access information with the user for the user to use to access a server storing files comprising records associated with the user in a computer readable storage medium, providing the user with a user interface on a computing device to remotely access the records stored on the server, receiving at the server the files comprising records associated with the user from a service provider associated with the user, receiving at the server a request from the user made through the user interface of the computing device for access to the files, wherein the access information is associated with the request, and sending the user a file containing the records associated with user from the server to the computing device in response to the request.

15 Claims, 15 Drawing Sheets

U.S. PATENT DOCUMENTS

| | | | |
|---|---|---|---|
| 5,924,074 A | 7/1999 | Evans | |
| 5,926,526 A | 7/1999 | Rapaport et al. | |
| 5,970,463 A | 10/1999 | Cave et al. | |
| 5,974,124 A | 10/1999 | Schlueter, Jr. et al. | |
| 5,997,476 A | 12/1999 | Brown | |
| 6,000,828 A | 12/1999 | Leet | |
| 6,032,119 A | 2/2000 | Brown et al. | |
| 6,073,106 A | 6/2000 | Rozen et al. | |
| 6,082,776 A | 7/2000 | Feinberg | |
| 6,088,677 A | 7/2000 | Spurgeon | |
| 6,223,559 B1 | 5/2001 | Coleman | |
| 6,463,417 B1 | 10/2002 | Schoenberg | |
| 6,574,484 B1 | 6/2003 | Carley | |
| 6,725,200 B1 | 4/2004 | Rost | |
| 6,738,784 B1 | 5/2004 | Howes | |
| 6,845,448 B1 | 1/2005 | Chaganti et al. | |
| 6,871,214 B2 | 3/2005 | Parsons et al. | |
| 6,941,271 B1 | 9/2005 | Soong | |
| 6,988,075 B1 | 1/2006 | Hacker | |
| 7,257,967 B2 | 8/2007 | Rheinstein | |
| 7,306,560 B2 | 12/2007 | Iliff | |
| 7,428,494 B2 | 9/2008 | Hasan et al. | |
| 7,440,904 B2 | 10/2008 | Hasan et al. | |
| 7,475,020 B2 | 1/2009 | Hasan et al. | |
| 7,509,264 B2 | 3/2009 | Hasan et al. | |
| 7,533,030 B2 | 5/2009 | Hasan et al. | |
| 7,707,047 B2 | 4/2010 | Hasan et al. | |
| 7,720,691 B2 | 5/2010 | Hasan et al. | |
| 8,131,563 B2 | 3/2012 | Hasan et al. | |
| 2001/0041991 A1* | 11/2001 | Segal et al. | 705/3 |
| 2002/0046061 A1 | 4/2002 | Wright et al. | |
| 2002/0059587 A1 | 5/2002 | Cofano et al. | |
| 2002/0077861 A1 | 6/2002 | Hogan | |
| 2002/0103675 A1 | 8/2002 | Vanelli | |
| 2002/0120470 A1 | 8/2002 | Trice, Sr. | |
| 2002/0128865 A1 | 9/2002 | Alten | |
| 2002/0178631 A1 | 12/2002 | Morton | |
| 2002/0189146 A1 | 12/2002 | Lyon | |
| 2003/0014282 A1 | 1/2003 | Haaksma et al. | |
| 2003/0037065 A1 | 2/2003 | Svab | |
| 2003/0040940 A1 | 2/2003 | Nehammer | |
| 2003/0059751 A1 | 3/2003 | Welles | |
| 2003/0086591 A1 | 5/2003 | Simon | |
| 2003/0098356 A1 | 5/2003 | Gombar | |
| 2003/0132132 A1 | 7/2003 | Small | |
| 2003/0140044 A1* | 7/2003 | Mok et al. | 707/10 |
| 2003/0208382 A1 | 11/2003 | Westfall | |
| 2003/0226889 A1 | 12/2003 | Morrison, Jr. | |
| 2003/0229452 A1 | 12/2003 | Lewis et al. | |
| 2003/0233844 A1 | 12/2003 | Rheinstein | |
| 2004/0078229 A1 | 4/2004 | Gay et al. | |
| 2004/0162895 A1* | 8/2004 | Mok et al. | 709/223 |
| 2004/0228336 A1 | 11/2004 | Kung et al. | |
| 2004/0267572 A1 | 12/2004 | Emery et al. | |
| 2005/0165285 A1 | 7/2005 | Iliff | |
| 2005/0209891 A1 | 9/2005 | Jacobus et al. | |
| 2005/0251423 A1 | 11/2005 | Bellam et al. | |
| 2006/0004588 A1 | 1/2006 | Ananda | |
| 2007/0061169 A1 | 3/2007 | Lorsch | |
| 2007/0061170 A1 | 3/2007 | Lorsch | |
| 2009/0007237 A1 | 1/2009 | Lorsch | |

FOREIGN PATENT DOCUMENTS

| | | |
|---|---|---|
| JP | 9218902 | 8/1997 |
| JP | 2001350847 | 12/2001 |

OTHER PUBLICATIONS www.linxcom.com, Jan. 7, 2005, obtained from Internet Archive Wayback Machine (www.archive.org), linxconnect.htm, linxconnect_faq.htm.

http://web.archive.org/web/20050909014053/http://www.mbox.com.au, "mBox—Unified Messaging", printed off of Internet Aug. 11, 2009, 1 page.

MyMedicalRecords.com, Inc., PCT/US06/04867, Notification of Transmittal of International Preliminary Examination Report dated May 17, 2010.

* cited by examiner

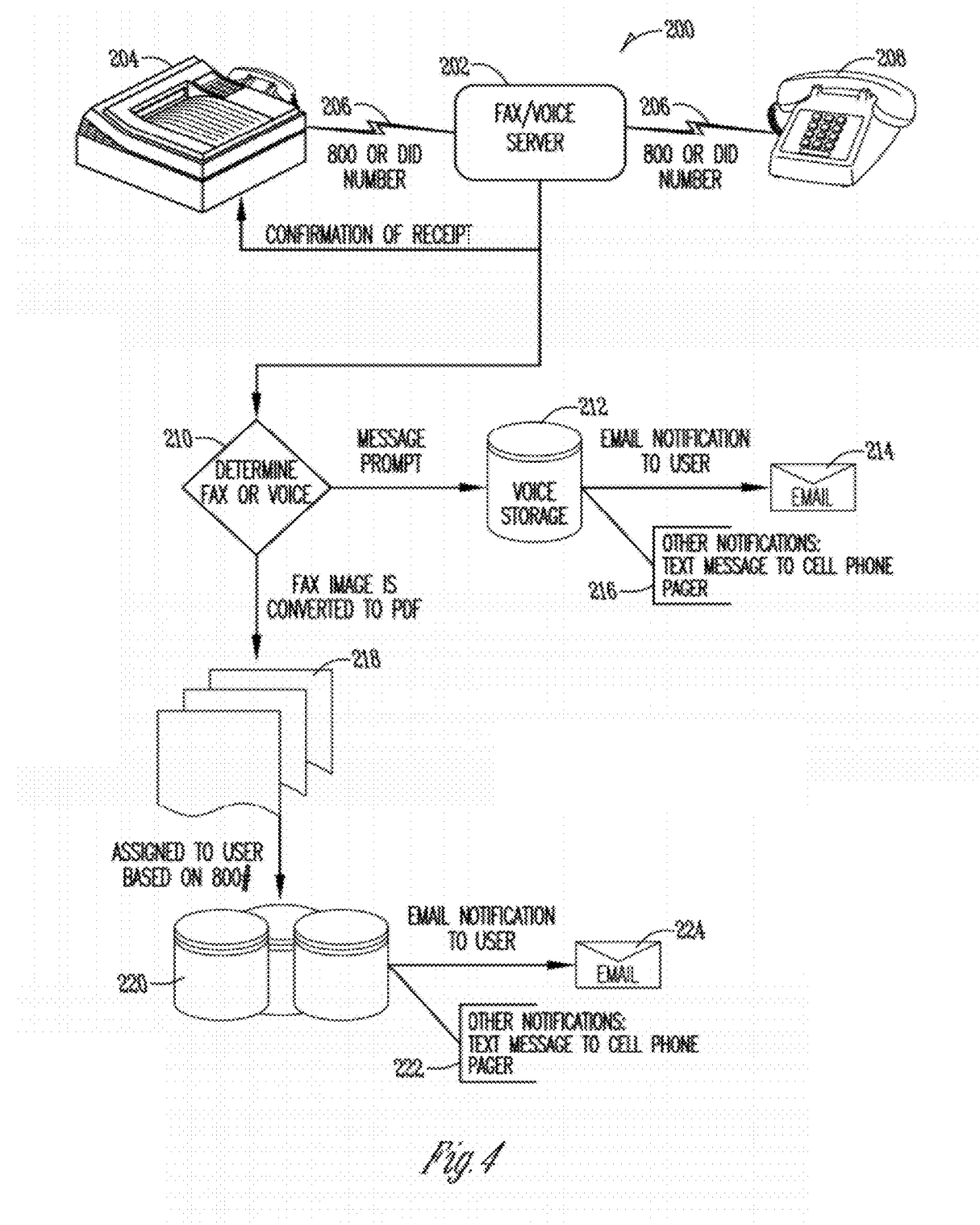

In Case of Emergency Please Contact
Name _____
Phone _____ Relationship _____
Secret question or Passcode _____
Name _____
Phone _____ Relationship _____
Secret question or Passcode _____
Current Medications _____

Allergies _____

Blood Type _____
Medical Conditions _____

Fig. 14

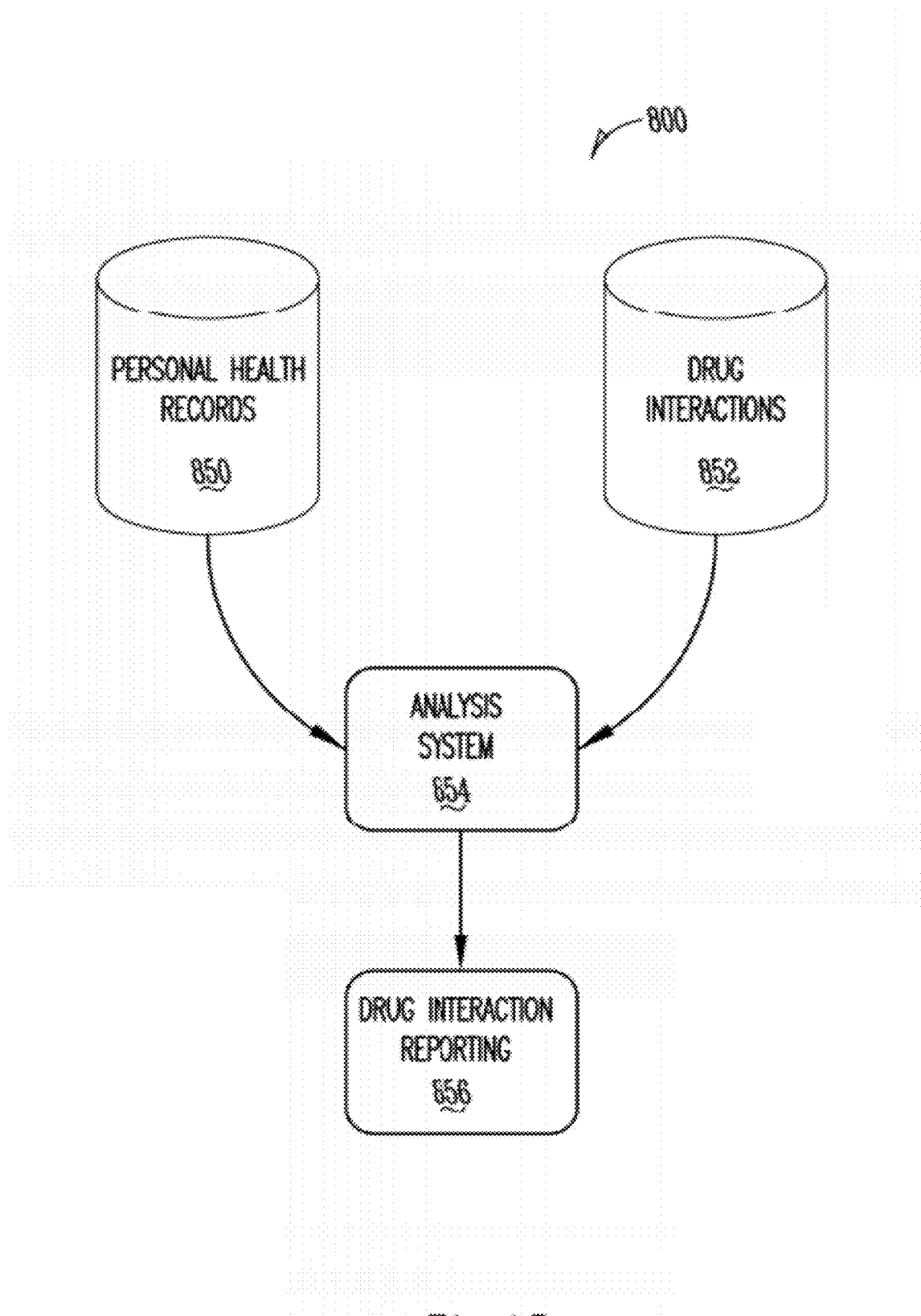

METHOD AND SYSTEM FOR PROVIDING ONLINE RECORDS

PRIORITY STATEMENT

This application is a Continuation application of U.S. Ser. No. 12/204,465 filed Sep. 4, 2008 which is a Continuation of U.S. Ser. No. 11/305,685 filed Dec. 16, 2005 which is a Continuation-in-part of, and claims priority to, U.S. patent application Ser. No. 11/225,518, filed Sep. 12, 2005, all of which are hereby incorporated by reference in their entirety.

BACKGROUND OF THE INVENTION

The present invention relates to the provision of online records. More particularly, the present invention relates to providing a means for consumers to request their medical records from healthcare providers, store their medical records, and provide for private communications between the consumers and their healthcare providers.

Medical and other health information can be particularly sensitive communications. Laws such as the HIPAA Privacy Rule restrict, limit, or place specific conditions on the dissemination of medical records. Laws such as the Health Insurance Portability and Accountability Act (HIPAA) provide a patient with the right to access to their own medical records.

A health provider, such as a hospital may require a patient to submit to their own privacy practices as a condition for treatment or admittance. A privacy practice statement by the health provider will likely explain that the patient has the right to inspect and copy their medical records, but there may be significant procedural hurdles to overcome that burden both the health provider and the patient. For example, the patient may be required to provide a written request, there may be processing delays in receiving copies of the medical or health related records, and the patient may incur additional processing charges resulting from the inconvenience created for the health provider to comply with the procedural hurdles that they put in place to avoid inappropriately disclosing records of their patients.

Of course, privacy concerns regarding a patient's medical records creates other problems for healthcare providers. For example, suppose a healthcare provider needs to communicate with a patient over the phone to check on a patient, request additional information regarding a patient's current condition, to schedule a test, report the results of a test, express the need for a return visit, or for other reasons related to providing health care to the patient. The healthcare provider calls the patient at home or at work and the patient is not available. Instead, the phone is answered by another person who could be a co-worker or family member. Alternatively, the healthcare provider is provided with the opportunity to leave a voicemail message. The healthcare provider must be very cautious to avoid inadvertently disclosing private information. Thus, the healthcare provider may not be able to leave a message with another person or with a voicemail system if doing so would violate the patient's privacy rights or expectations of privacy. Even in cases where the healthcare provider may be legally authorized to do so via a previously agreed upon privacy policy, doing so may be against the person's wishes as they did not understand what they were consenting to when they consented to the privacy policy or did not understand their rights under the privacy policy. A message for the patient may provide other parties with more information then the patient would want them to know. Even when a healthcare provider attempts to leave a seemingly innocuous message with a voicemail system or with another individual, more information may be shared then the patient wants to be shared. For example, a message left with another requesting that the patient call a particular doctor may be more than what the patient would want shared with others. For example, suppose it is known or readily determined that the doctor is an obstetrician and the patient is a woman who does not want her significant other to know she is pregnant yet. Suppose it is known or readily determined that the doctor is an oncologist and the patient does not want their co-workers or employer to know that the patient has cancer. Mere knowledge of the doctor's name, in these cases would be sufficient to make an educated guess about the patient's condition or potential condition. A patient may consider this a violation of their privacy. Regardless of whether or not the patient has any legal recourse, this can result in the patient being upset and can have a negative impact on the relationship between the patient and their healthcare provider.

Of course, instead of leaving a message, a healthcare provider could simply call back, but this is inconvenient for the healthcare provider or their staff and may unduly delay the amount of time before the patient receives the message. Thus, private and secure communications would benefit both the healthcare provider and the patient. The healthcare provider would not have to worry about disclosing private information to a party who should not have the information. And, the patient would be more likely to receive the communications sooner and could take comfort knowing that their privacy was maintained.

Another problem relating to medical records is that where an individual sees multiple healthcare providers, the inconvenience of requesting medical records is multiplied. Given the inconvenience and the potential delay in obtaining records it is also likely that in such instances the individual does not actually compile a complete medical history. To the extent the individual has their records, the individual must determine a method of storing and organizing them.

Yet another problem relating to medical records is that often times they are most needed at a time when the individual is unable to provide them. For example, in emergency situations it would be desirable for caregivers to know and understand the individual's medical history. Knowledge of specific allergies may be essential to avoid administration of medications that would adversely impact the condition of the individual. Knowledge of pre-existing conditions may be essential to correct diagnosis and treatment. What is desired is a way that relevant medical records could be shared when needed most.

Various attempts have been made to assist consumers with their medical records in different ways. One example of such an attempt is Synchart. Synchart is a web-based service (www.synchart.com) that allows consumers to enter their personal and family health information into a database. Users can enter doctor visits, immunizations, hospital visits, allergies, and other relevant information and generate reports based on the data entered. As part of the services, consumers receive a CD with their medical information data, as well as a wallet card. Because medical data is stored on the Synchart web server, user health information is accessible from any Internet-connected computer, which Synchart claims will allow doctors and other providers to access user information if the user gives them account information.

One of the problems with a service such as Synchart is that it requires users to enter information about their health histories into a database, a time consuming and cumbersome process which is inconvenient and sometimes difficult. These issues are further magnified if an individual does not have a complete understanding of their medical records. Another problem of such a system is that clerical errors by the user can result in the user's medical records having inaccurate information. A further problem is that medical information is not immediately available if the individual does not immediately enter the information. Such a problem is exacerbated by the fact that often times when an individual is frequently seeing healthcare providers they are ill or injured and it is particularly inconvenient for them to update their medical records. Finally, such a system does not address issues of obtaining the medical records from the healthcare provider.

Redi-Records is another example of a system that assists consumers with obtaining access to their medical records. For a fee, Redi-Records will gather all of a subscriber's medical records from different doctors and hospitals. Once the records are gathered, Redi-Records will digitize them and put them onto two mini-CDs. Users can carry 1 mini-CD in their wallet and keep one at home. For an additional cost, the company will update a user's records every 180 or 90 days. Such a service is marketed with the promise that having records on a mini-CD will make it easier for you to receive proper treatment in the event of a medical emergency. One of the problems with such an approach is that the records are not necessarily current. Another problem with such an approach is that a third party is involved so that complex forms will need to be completed by the consumer and the consumer's providers in order to grant the third party access to the medical records which could cause delay in gathering information. Due to the third party involvement, there is a chain of human handling of the documents that could compromise the privacy of the documents. In addition, the mini-CDs may not be secured or password protected, or the information about how to access them readily available. Where the mini-CDs are not secured or password protected, unauthorized individuals could access a person's medical records.

Another prior art approach is HeartRecord (www.heartcenteronline.com). This services focuses on cardiac patients. Users pay a subscription fee and are able to enter information about their medical history, doctors, and prescriptions into a database that is accessible using the Internet and a secured password. As a result, important information is available in the event of a medical emergency or when users visit a doctor. HeartRecord also allows users to upload their EKGs and other vital images to their account either from a computer, or by e-mailing, faxing or mailing the image to the company. HeartRecord has several inherent problems. HeartRecord's system places the onus of entering data and uploading images completely on the user. HeartRecord's system fails to contemplate the user's possible unfamiliarity with entering data and uploading images. It also assumes the user will keep their record current by practicing the utmost diligence in updating new data and images to their account. Another problem with such as service is that it is limited in scope. A further problem with such as system is that it does not create a private communications link between a doctor and patient.

Another prior art approach is demonstrated by Personal MD. This product (www.personalmd.com) uses a fax-based technology to allow users to store records that can be accessed via the Internet. Personal MD also offers a feature where users can file the most critical information in a folder marked "Emergency", which can be printed out by personnel via fax in the event of a medical crisis. Personal MD also offers medication reminders and other calendar features, and the site includes syndicated health information content. One of the problems with this approach is difficulty of use. For example with Personal MD, a non-dedicated number is used thus the person sending a fax must enter a PIN before sending the fax. This can create an unacceptable inconvenience for a busy doctor's office and can cause frustration. Moreover, it also creates an additional opportunity for human error in that use of the wrong pin number may direct the fax to a wrong destination. Furthermore, the non-dedicated number may be busy more often than not, adding to the frustration of updating or accessing the user's medical records. Such a system is not focused on providing a private communications link between a patient and their healthcare provider.

Another prior art approach is Web MD Health Manager offered by WebMD (www.webmd.com). This system allows users to enter data about their personal health such as health conditions, blood pressure, cholesterol level and other metrics. This system will then run those numbers against a database to provide a personal "self-assessment" and provide tips on better health. Such a system does not provide for storage of medical records or a private communications links between a healthcare provider and patient.

Another prior art approach is available from iHealthRecord.org. This service provides an interactive data entry screen that allows users to enter their personal and family health histories. This information can then be printed out on a wallet card. One of the problems with such an approach is that it requires users to enter information on their medical records into a database, a time consuming and cumbersome task which assumes the user will be diligent in updating their health history, but even so may result in inaccuracies. In addition, this approach does not provide a secure communications link between a healthcare provider and their patient or offer storage and management of personal health and medical records.

Another example of a prior art approach is disclosed in U.S. Patent Application Publication No. 2004/0267572 to Emery et al. Emery is directed towards a system for an online database for personal, medical, appointment and other information. Emery also discloses providing patients with emergency information ID cards which provide information that can be used to access the online database. The system of Emery requires either the patient or the healthcare provider to access the online database and modify the online health records. Thus, such a system is cumbersome to use, requiring patients to either enter their own information without error in a timely fashion or require healthcare providers to add yet another additional service which would require additional time, resources, and familiarity or training with the system.

Another prior art approach is disclosed in U.S. Patent Application Publication No. 2005/0209891 to Jacobus et al. Jacobus discloses organizing and aggregating medical records, clinical observations, and medical imagery into a common database which is accessible over the web. Jacobus also allows providers to upload or update patient records and patients to request that their information be uploaded. Such a system requires the healthcare provider's use of the system and involvement in the process. Thus, a patient would be unable to fully benefit from such a system without all of their healthcare providers using the same system, which their healthcare providers may not be willing or able to do, particularly given the added time and costs which would be associated with using such a system.

Another prior art approach is disclosed in U.S. Patent Application Publication No. 2005/0251423 to Bellam et al. Bellam discloses a programmable rules-based interface between a patient and an electronic medical record (EMR) which allows controlled patient access to the EMR to increase patient participation in the healthcare process. Bellam actually limits a patient's access to their own data. In addition, Bellam does not address the problems of obtaining a complete and accurate EMR.

Thus, despite the advancements in these areas, problems remain. In particular, there is a general lack of recognition of the need to provide secure and private communications between a healthcare provider and their patient and to do so in a manner that is convenient to both the healthcare provider and the patient. There is also a general lack of recognition of the problems for an individual to exercise their rights to receive access to their healthcare records and be able to store and maintain those records in one secured, password protected account that allows for files to be organized.

BRIEF SUMMARY OF THE INVENTION

Therefore it is a primary object, feature, or advantage of the present invention to improve upon the state of the art.

It is a further object, feature, or advantage of the present invention to facilitate health care personnel's compliance with HIPAA or other legal requirements regarding privacy of medical records.

A still further object, feature, or advantage of the present invention is to provide an individual with meaningful access to their healthcare records thereby allowing the individual to exercise their legal rights with respect to controlling access to their medical records.

Yet another object, feature, or advantage of the present invention is providing individuals with immediate access to healthcare records in emergency situations to assist in providing appropriate care.

A further object, feature, or advantage of the present invention is to provide a convenient and cost effective method for healthcare providers to comply with laws regarding privacy of healthcare records.

A still further object, feature, or advantage of the present invention is to provide a convenient and cost effective method for individuals to request that their healthcare providers provide copies of medical records.

Another object, feature, or advantage of the present invention is to provide a private communications link between healthcare personnel and their patients.

Yet another object, feature, or advantage of the present invention is to provide for placing an individual in control of their medical records and allowing them to selectively provide access to others.

A still further object, feature, or advantage of the present invention is to facilitate storing all of an individual or family's medical records and related information in a single location so that healthcare personnel can be given complete medical information/history when needed or analysis can be performed on the medical records.

Another object, feature, or advantage of the present invention is to provide a means for individuals to create calendars to remind them of the need to refill prescriptions.

Yet another object, feature, or advantage of the present invention is to provide a means for individuals to create calendars to maintain doctor's appointments.

A further object, feature, or advantage of the present invention is to provide reminder messages regarding the need to refill prescriptions or remember doctor's appointments.

A still further object, feature, or advantage of the present invention is to provide a method to store, organize, and annotate medical records and also to customize the storage by giving the user the ability to name the folders in which those records are stored.

Another object, feature, or advantage of the present invention is to give users the ability to upload images, such as x-rays or scans.

Yet another object, feature, or advantage of the present invention is to give users the ability to forward records via fax to a healthcare provider.

A further object, feature, or advantage of the present invention is to give users the ability to see if there are any possible interactions between prescription drugs they are taking.

A further object, feature, or advantage of the present invention is to provide a means for individuals to store and access not only medical records, but other types of health records including dental records, healthcare records associated with pets, and vital documents, including, without limitation, wills, living wills, a power of attorney, and a healthcare power of attorney.

Yet another object, feature, or advantage of the present invention is to allow for the healthcare provider to quickly and easily, yet securely, communicate records associated with an individual to the individual.

One or more of these and/or other objects, features, or advantages of the present invention will become apparent from the specification and claims that follow.

According to one aspect of the present invention, a method for providing a consumer with the ability to access and collect personal health records associated with the consumer is provided. The method includes assigning a phone number individually associated with the consumer for fax and voice communications from a healthcare provider and associating access information with the consumer for the consumer to use to access a secure web site. The consumer is provided with a document to provide to the healthcare provider exercising legal rights of the consumer for access to the health records, the document requesting the healthcare provider to send the health records to the phone number. The method further provides for receiving a private fax communication comprising a personal health record associated with the consumer for which the consumer has requested and given permission to the healthcare provider to send, converting the private fax communications into an image file format (such as a PDF), storing the health record encoded in the image file format, and providing the consumer with secure access to the web site using the access information and providing on the web site an interface to the health records of the consumer for the consumer to access the health record.

The document may include an adhesive or be a sticker so that it can be easily attached to the health records. An emergency access card which includes access information and can be used by a third-party to access the health record associated with the consumer in the event of a medical emergency associated with the consumer can also be provided.

The web site interface preferably allows for organizing health records into separate file folders with functionality for the consumer to name the file folders and add file folders as well as provide additional password protection for the file folders.

According to another aspect of the present invention a kit is provided for assisting a customer with exercising rights to health records associated with the customer, accessing the health records, maintaining the health records as private, and providing access to the health records in case of emergency. The kit includes an access card comprising access information associated with the customer to be used to access a secure web site providing access to health records of the customer to be used to convey the access information to another in event of a medical emergency associated with the customer. The kit also includes at least one sticker exercising legal rights of the customer to healthcare records and comprising instructions to a healthcare provider to electronically send the health records to a destination and wherein the health records sent to the destination are accessible on the secure web site.

According to one aspect of the present invention, a method is provided for providing a user with the ability to access and collect records associated with the user in a secure and private manner. The method includes assigning a phone number to the user for private fax and voice communications from service providers, associating access information with the user for the user to use to access a web site, receiving a private fax communication comprising a record associated with the user for which the user has requested and given permission to the service provider to send to the phone number; converting the private fax communications into an image file format, storing the record encoded in the image file format, providing the user with access to the web site using the access information and providing on the web site an interface to the records of the user for the user to access the record, and wherein the web site interface further provides for organizing and annotating the records by the user into separate file folders with functionality for the user to name the file folders and add file folders.

According to another aspect of the present invention a, kit is provided for assisting a user with exercising rights to records associated with the user and created by a service provider, accessing the records, maintaining the records as private, and providing access to the records in case of emergency. The kit includes an access card comprising access information associated with the user to be used to access a secure web site providing access to records of the user to be used to convey the access information to another in event of an emergency associated with the user and at least one document comprising a request to a service provider to electronically send the records to a destination and granting permission by the user to the service provider to electronically send the records to the destination and wherein the records sent to the destination are accessible on the secure web site.

According to another aspect of the present invention a system for communicating records of a user, the system includes a consent document providing instructions for and giving permission to a service provider to fax records of a user to a dedicated phone number associated with the user, a fax server for receiving faxes of the records directed to the dedicated phone number, a web server in operative communication with the fax server and adapted to provide a secure web-based interface to the records, and wherein the web-based interface provides for organizing and annotating the records by the user into separate file folders with functionality for the user to name the file folders and add file folders.

According to another aspect of the present invention, a method for providing a user with the ability to access and collect records associated with the user in a private manner is provided. The method includes assigning a destination address associated with a user for private fax communications from a service provider, associating access information with the user for the user to use to access a web site, receiving a private fax communication comprising a record associated with the user for which the user has requested and given permission to the service provider to send to a fax number, converting the record into an image file format, storing the record encoded in the image file format, associating the record encoded in the image file format with a user account of the user, and providing the user with access to the user account on the web site using the access information. The web site provides an interface to the user for organizing and annotating the into separate file folders with functionality for the user to name the file folders and add file folders.

According to another aspect of the present invention, a method for providing a user with functionality for accessing and collecting records associated with the user is provided. The method includes associating access information with the user to use to access a web site, receiving a record encoded in an image file format from a service provider, automatically determining a user account associated with the record and associating the record with the user account, and providing the user with access to the user account on the web site using the access information. The record encoded in the image file format is a representation of a faxed communication from the service provider.

According to another aspect of the present invention, a method for providing a user with the ability to access and collect records associated with the user in a secure and private manner is provided. The method includes assigning an identifier to the user for private fax and voice communications from service providers, associating access information with the user for the user to use to access a web site, receiving a plurality of private fax communications from different providers, each of the private fax communications comprising a record associated with the user for which the user has requested and given permission to the service provider to send to the phone number, converting the private fax communications into image file formats, storing the records encoded in the image file formats, and providing the user with access to the web site using the access information and providing on the web site an interface to the records of the user for the user to use to access the record. The interface provides for organizing the records into folders, creating additional folders, and naming the folders.

BRIEF DESCRIPTION OF THE DRAWINGS

FIG. 4 is a diagram illustrating one embodiment of a system of the present invention.

FIGS. 13 and 14 are pictorial representations of a preferred embodiment of a wallet card which can be used according to the present invention.

FIG. 15 is diagram illustrating one embodiment of drug interacting reporting and analysis of the present invention.

DETAILED DESCRIPTION OF THE PREFERRED EMBODIMENT

The present invention provides for a convenient method for individuals to collect and store their private medical information and to provide private communications between the individual and their healthcare providers. One of the ways that the present invention collects and stores private medical information and facilitates private communications is through use of a LIFELINE which is a dedicated toll-free number for fax and voice communications. This dedicated toll-free number provides direct and private communications between a healthcare provider and their patient so that a healthcare provider can be assured that they are maintaining patient communications in secret and to avoid violating applicable privacy laws or patient expectations regarding privacy.

Figure 1:
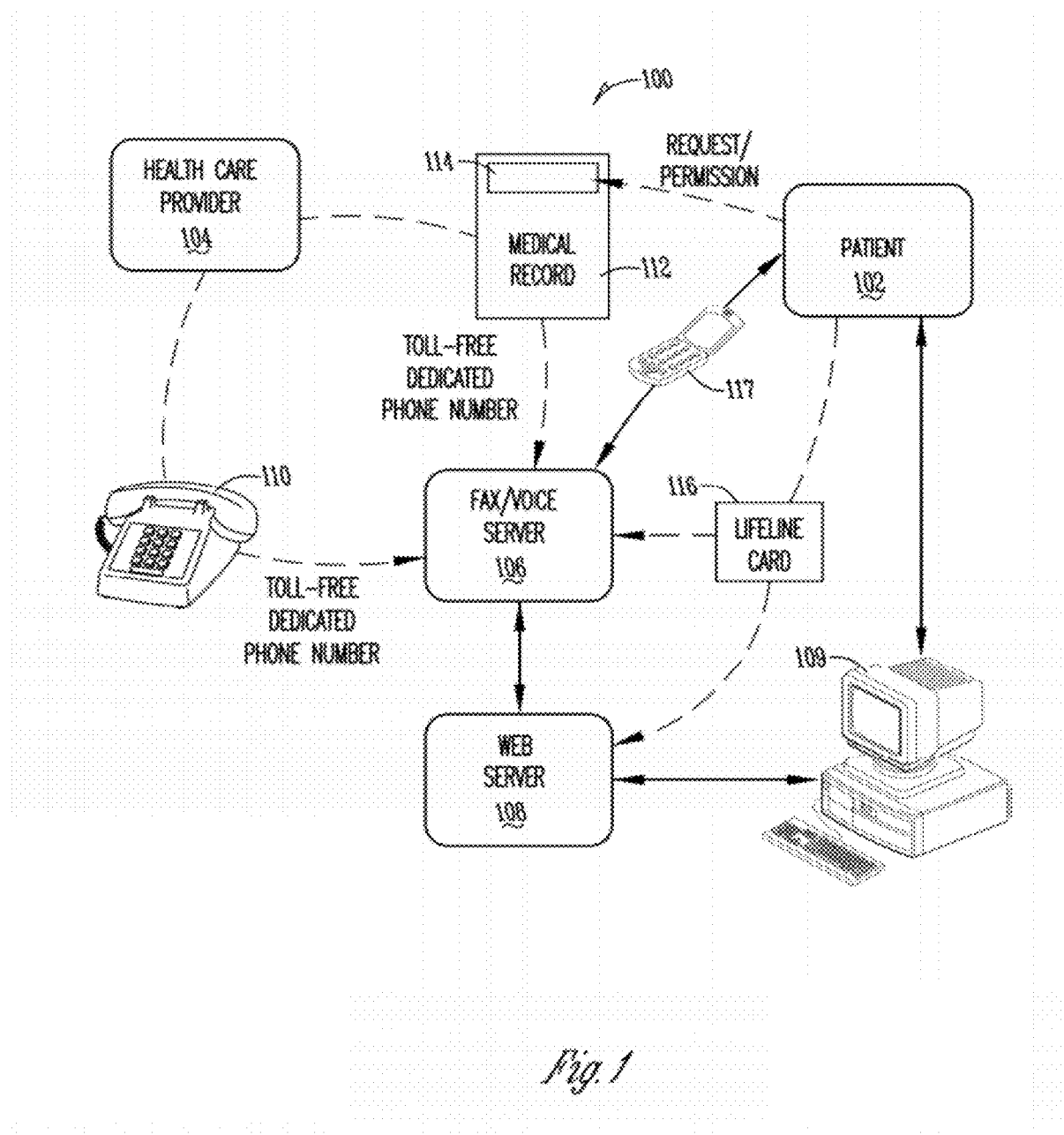
FIG. 1 is diagram illustrating one embodiment of a system of the present invention.

FIG. 1 is a diagram illustrating one embodiment of a system 100 of the present invention. In FIG. 1, a consumer or patient 102 is shown. A healthcare provider 104 is also shown as well as a fax/voice server 106. A web server 108 is operatively connected to the fax/voice server 106. The healthcare provider 104 uses the phone 110 to communicate private voicemail messages through a toll-free dedicated phone number to the fax/voice server 106. In addition, the healthcare provider faxes health or medical records 112 to the fax/voice server 106 using the toll-free dedicated phone number. The medical record 112 preferably has a sticker 114 present on the medical record 112. The sticker 114 indicates or instructs the healthcare provider 104 or their staff to fax the information to the toll-free dedicated phone number. In addition, the sticker 114 provides an indication of clear consent from the patient 102 to the healthcare provider 104 to the toll-free dedicated phone number. Thus, it becomes a simple process for a consumer or patient 102 to provide their healthcare provider 104 with instructions to fax health records, a simple process for the healthcare provider 104 to obtain permission to fulfill a request for healthcare records, and a simple process for the healthcare provider 104 to do so in a secure and convenient manner as the fax is going directly to a toll-free dedicated phone number associated with the patient 102.

The web server 108 is operatively connected to the fax/voice server 106 such as over a network or otherwise. A patient 102 or their proxy can communicate directly with the web server 108 through a computing device 109 or the fax/voice server 106 using a phone 117. The patient 102 can use a LIFELINE card 116 that contains access information to log on to the web server 108 associated with a web site of the present invention, or as a reminder of their toll free dedicated phone number which they can call to access voicemail messages, listen to text-to-speech conversion of emails, or otherwise access information.

The present invention also allows a patient 102 to upload files using a computing device 109 to the web server 108. In addition, the patient 102 can use the computing device 109 to interact with the web server 108 to specify that a prescription or other personal health record is faxed via the fax/voice server 106 to a healthcare provider 104.

Figure 2:
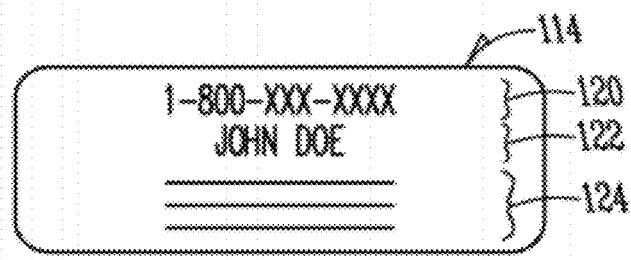
FIG. 2 is a pictorial representation of a sticker authorizing transmissions of records to the user account according to one embodiment of the present invention.

FIG. 2 illustrates one embodiment of a sticker 114 for a patient to give to their healthcare provider to request or instruct their healthcare provider to fax medical records to the toll free dedicated phone number associated with the patient. Although it is preferred that a sticker 114 be used because of the added convenience provided by being able to permanently or semi-permanently attach to a patient file at a healthcare providers office, the present invention contemplates that other types of documents could be used. The sticker 114 includes the LIFELINE phone number 120 which is the toll free dedicated phone number associated with the patient. Note that there is no pin number required which greatly simplifies the process of faxing documents. In addition, the name 122 of the patient is shown. There is also a written request 124 on the sticker 114 that instructs the healthcare provider to fax the records and explicitly gives permission to fax the healthcare record. The language of the written request 124 may vary as necessary to comply with any applicable laws. It should be appreciated that the sticker 114 provides great convenience to both an individual who wants to instruct their healthcare provider to give them access to their medical records as well as to the healthcare provider who can now easily provide the individual with access to their medical records. The present invention further contemplates that medical alert information can also be placed on the sticker 114. The types of medical alert information includes, without limitation, blood type information (i.e. ABO and Rhesus information), allergies to drugs, presence of a pacemaker, diabetes, epilepsy, or other conditions.

Figure 12:
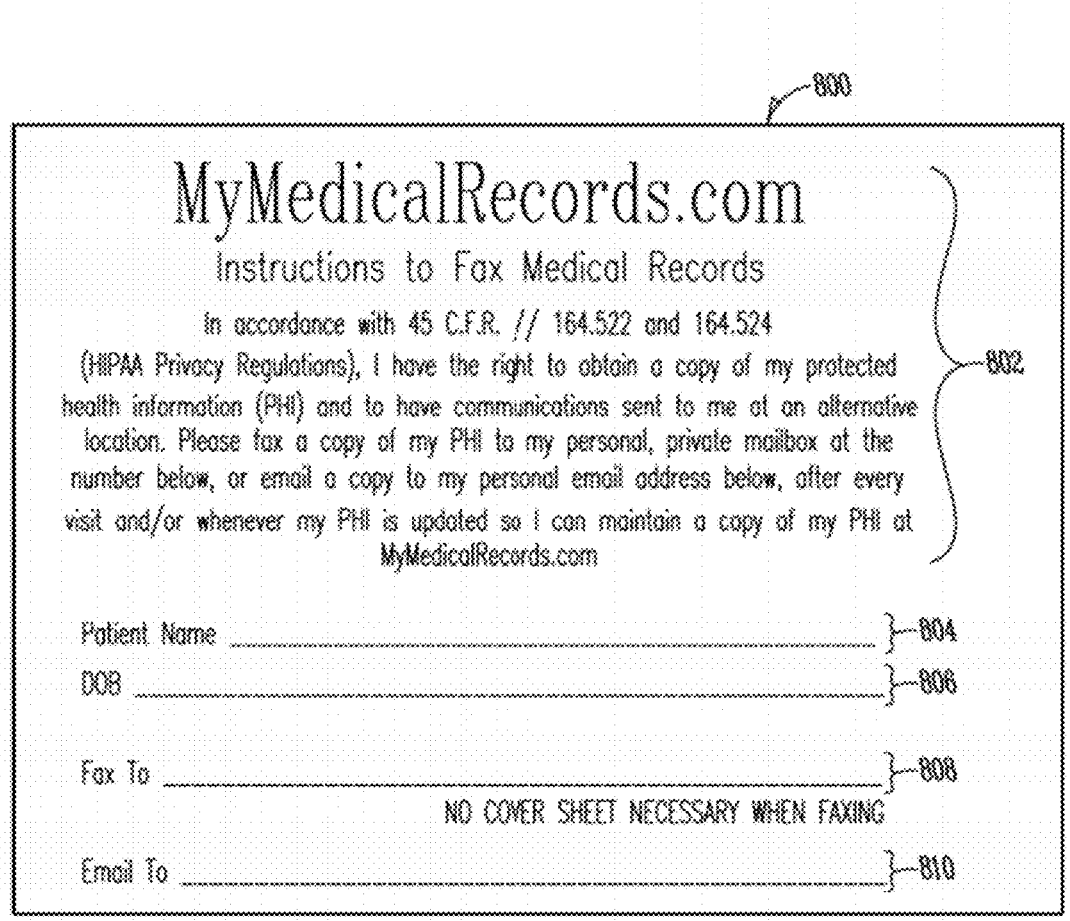
FIG. 12 is a pictorial representation of a preferred embodiment of a sticker providing instructions for faxing medical records.

FIG. 12 illustrates another embodiment of such a sticker. Note that in FIG. 12, a sticker 800 is shown. The sticker 800 includes instructions to fax or email medical records 802 which serve to exercise a patients rights under 45 C.F.R. §164.522 and 45 C.F.R. §164.524 (HIPAA Privacy Regulations) to obtain a copy of their protected health information (PHI) and to have such communications sent to the patient at an alternative location. In particular, the instructions 802 instruct the healthcare provider to fax a copy of the PHI to a personal, private mailbox at a toll-free or local number after every visit and/or whenever the PHI is updated so that the patient can maintain a copy of their PHI. Alternatively, the instructions 802 provide for instructing the healthcare provider to email the records to specified email address 810.

The sticker 800 includes a region 804 for the patient to print or type their name and a region 806 for the patient to print or type their date of birth. There is also a region 808 for the fax number to which medical records are delivered. Preferably, the number is a toll-free fax or local number assigned to the patient. There is also a region 810 for an email address to which the medical records are to be submitted.

Figure 3A:
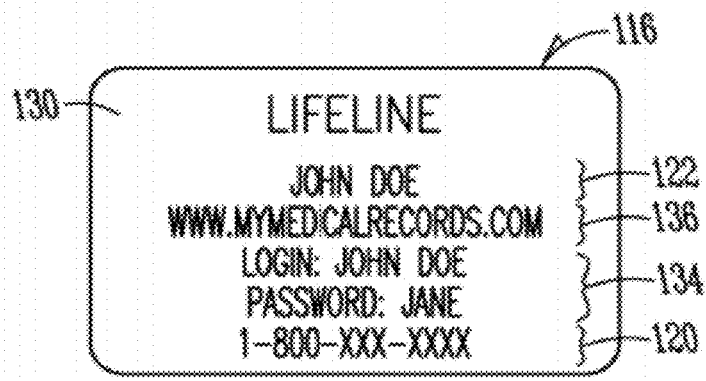
FIG. 3A and FIG. 3B illustrate a card with medical record access information according to one embodiment of the present invention.
Figure 3B:
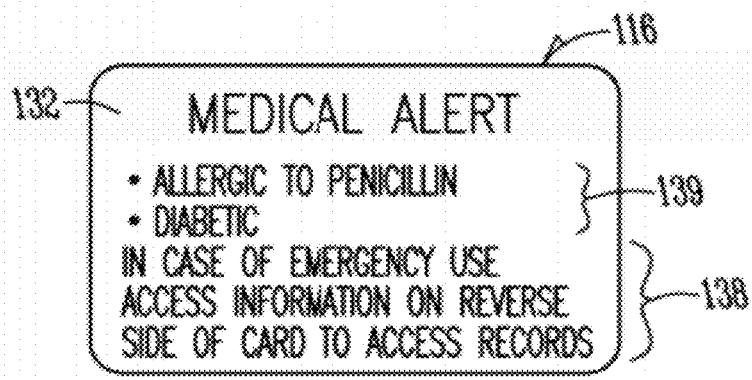

FIG. 3A and FIG. 3B illustrate one embodiment of a LIFELINE card 116. The LIFELINE card has a front side 130 and an opposite back side 132. The card 116 includes the name of the individual 122, a URL for a web site 136 which stores medical records for the individual. In addition there is access information 134 such a username and password. The card 116 also includes the toll free dedicated phone number 120 associated with the individual. On the back side 132 of the card 116 as best shown in FIG. 3B, medical alert information 139 is provided. The medical alert information 139 can include allergies which the individual has, medical conditions such as diabetes or epilepsy, the presence of a pacemaker, or other medical information that may be of great importance in evaluating or treating the individual in the case of a medical emergency. The medical alert information can further include blood type information (i.e. ABO and Rhesus information). Also, instructions 138 are provided on the card 116 to indicate how one could access complete medical records or information about the individual.

The present invention contemplates including the sticker 114 (or other permission/request document) and the LIFELINE card 116 in a welcome kit when an individual or family subscribes or signs-up for the service. In addition, from the web site associated with the service, preferably addition stickers and/or additional cards can be printed and information can be updated as necessary.

Figure 13:
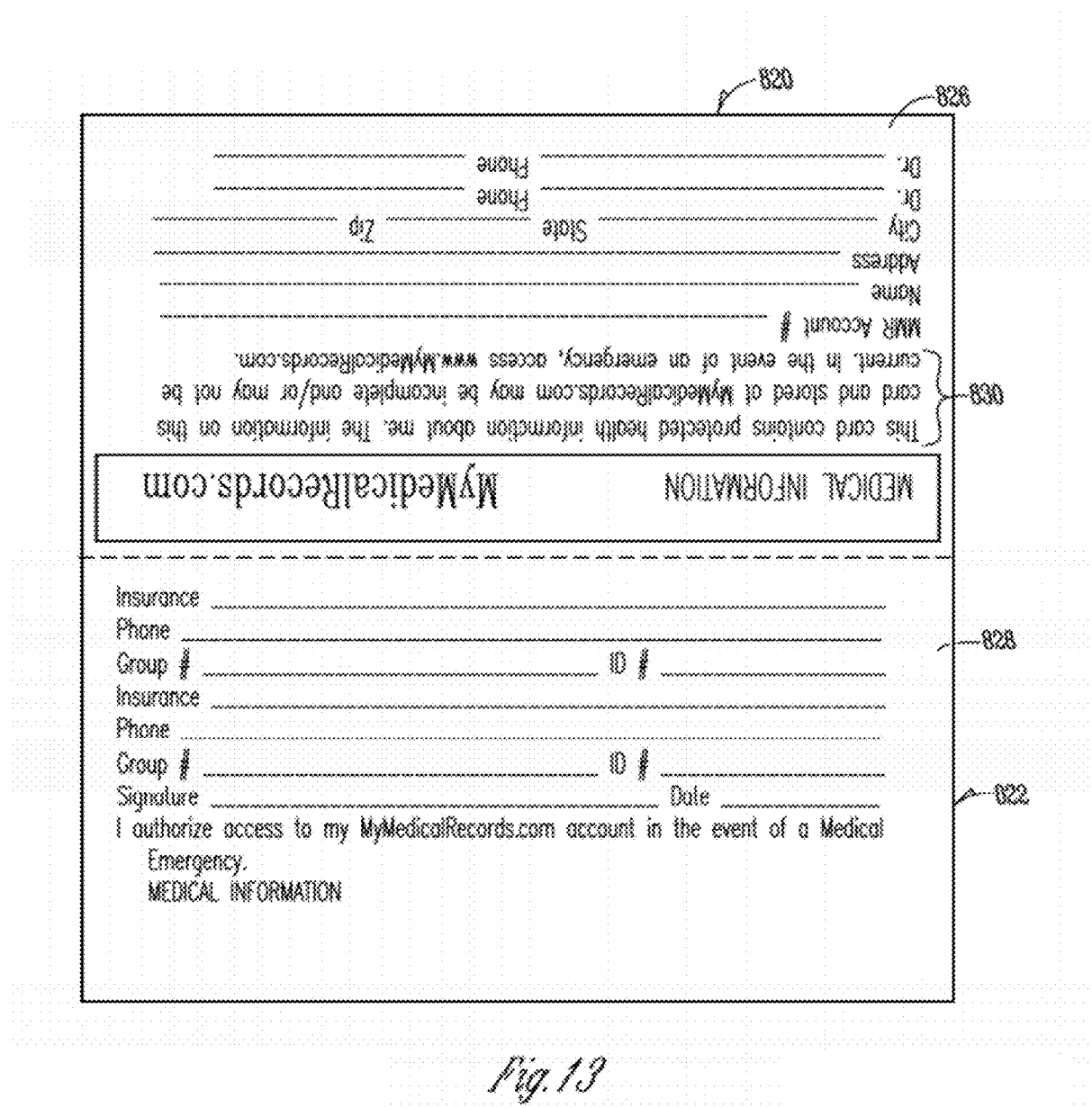

FIGS. 13 and 14 illustrate another embodiment of a wallet card of the present invention. The wallet card 820 includes a first side 822 and an opposite second side 824. As shown in FIG. 13, the first side 822 of the wallet card 820 has a first panel 826 and a second panel 828. The first panel 826 includes identifying information about an individual and emergency instructions 830. The emergency instructions 830 indicate that protected health information can be accessed, in an emergency, at a web site. The second panel 828 of the first side 822 of the wallet card 820 includes insurance information and signature of the patient.

As best shown in FIG. 14, the second side 824 of the wallet card 820 includes emergency contact information, including a secret question or passcode so that the emergency contact person can better verify that there is an emergency, and not a fraudulent notification. The second side 824 of the wallet card 820, also preferably includes information regarding current medications, allergies, blood type, and medical conditions which may be critical to providing appropriate emergency care.

FIG. 4 illustrates one embodiment of a system of the present invention. Preferably such a system is implemented using equipment from Prairie Systems, Inc. of Omaha, Nebr., although the present invention contemplates that other vendors may be used. As shown in FIG. 4, the system 200 includes a fax/voice server 202. The fax/voice server 202 is accessible by a fax machine 204 or a phone 208 through using a dedicated phone number 206. Preferably, the phone number 206 is toll-free as this increases the accessibility and convenience of the system which is very important. However, the phone number 206 could also be a direct dial phone number. When the fax/voice server 202 receives a call, a determination is made in step 210 as to whether the call is a voice call or a fax call. Where the call is a voice call, an interactive voice response (IVR) system is used to determine who the caller is, the purpose of the call, or other information, and then stores any voicemail message in voice storage 212. The system is adapted to notify the individual that there is a voicemail message through an email notification in step 214 and/or other types of notification in step 216. Other types of notification can include, but are not limited to text messages to a cell phone or pager. Thus, a healthcare provider can call the LIFELINE number 206 and leave a voicemail message for the individual and know that the communication is a private communication. Thus, the healthcare provider can leave private and confidential information, such as the results of a test, or the need to schedule a new appointment, or other information. The individual is alerted to the presence of the voicemail message and can then call-in to the fax/voice server 202 to check messages.

Where documents are faxed, fax images are collected and converted to portable document format (PDF) documents 218. Although, the PDF format is preferred, the present invention contemplates that other types of document conversions can be done as may be appropriate in a particular implementation of the present invention. Based on the dedicated phone number 206 used to send the documents, the faxed documents are assigned to a user account and stored in step 220. The individual is alerted via email that the documents have been sent in step 224. Alternatively, the individual is alerted via text messaging in step 222 that a fax has been sent.

Figure 5A:
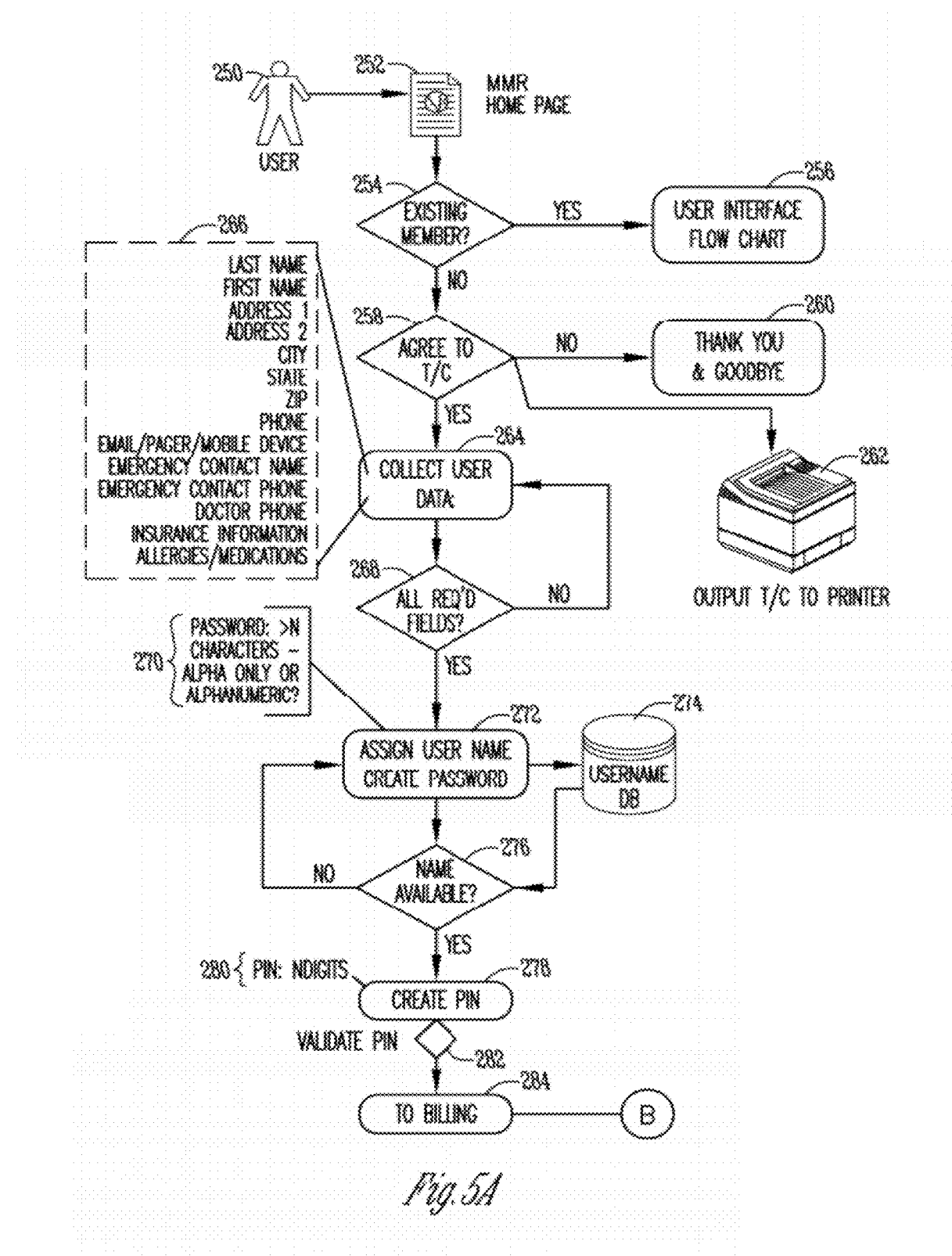
FIG. 5A and FIG. 5B are flow diagrams illustrating an enrollment process according to one embodiment of the present invention.
Figure 5B:
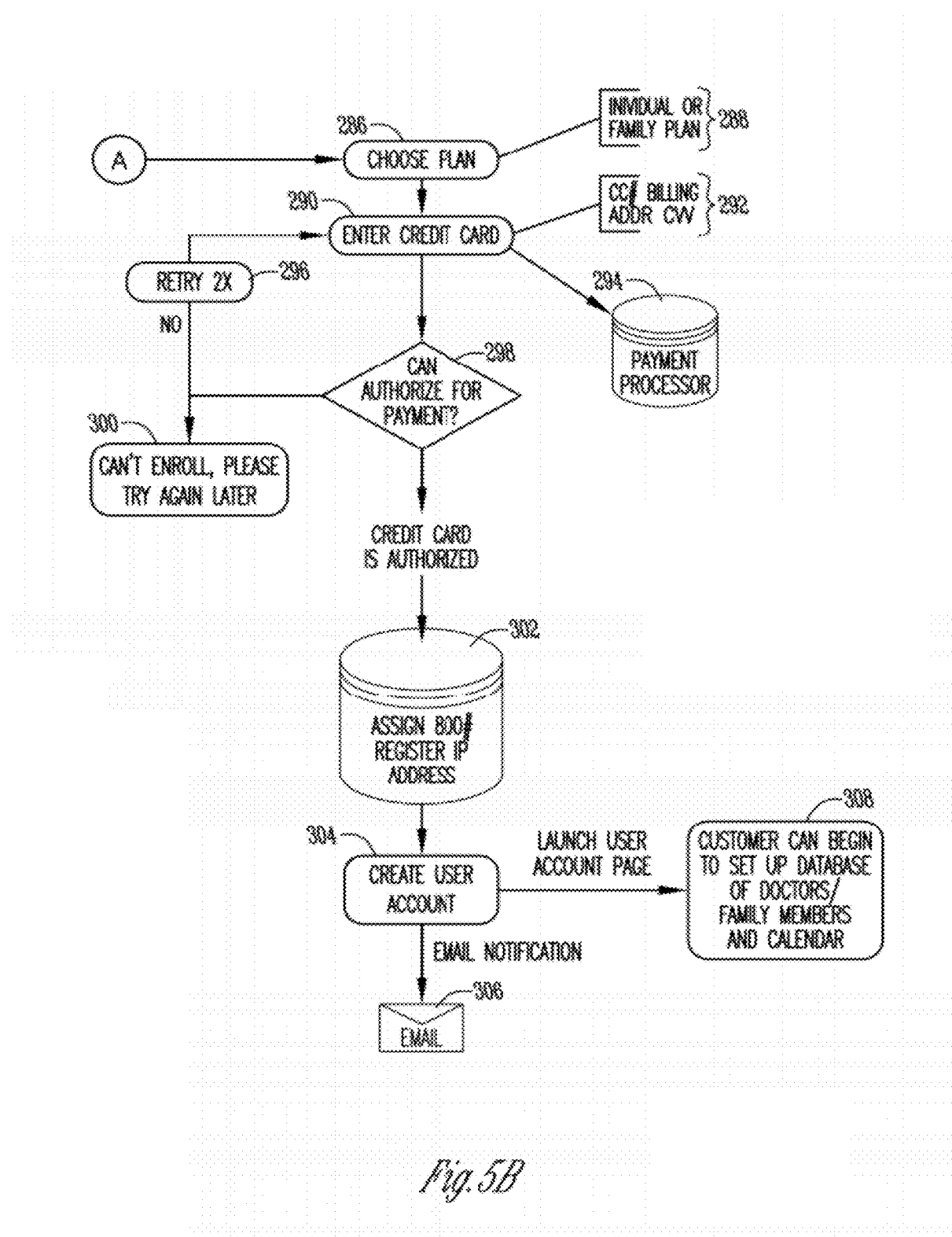
Figure 6:
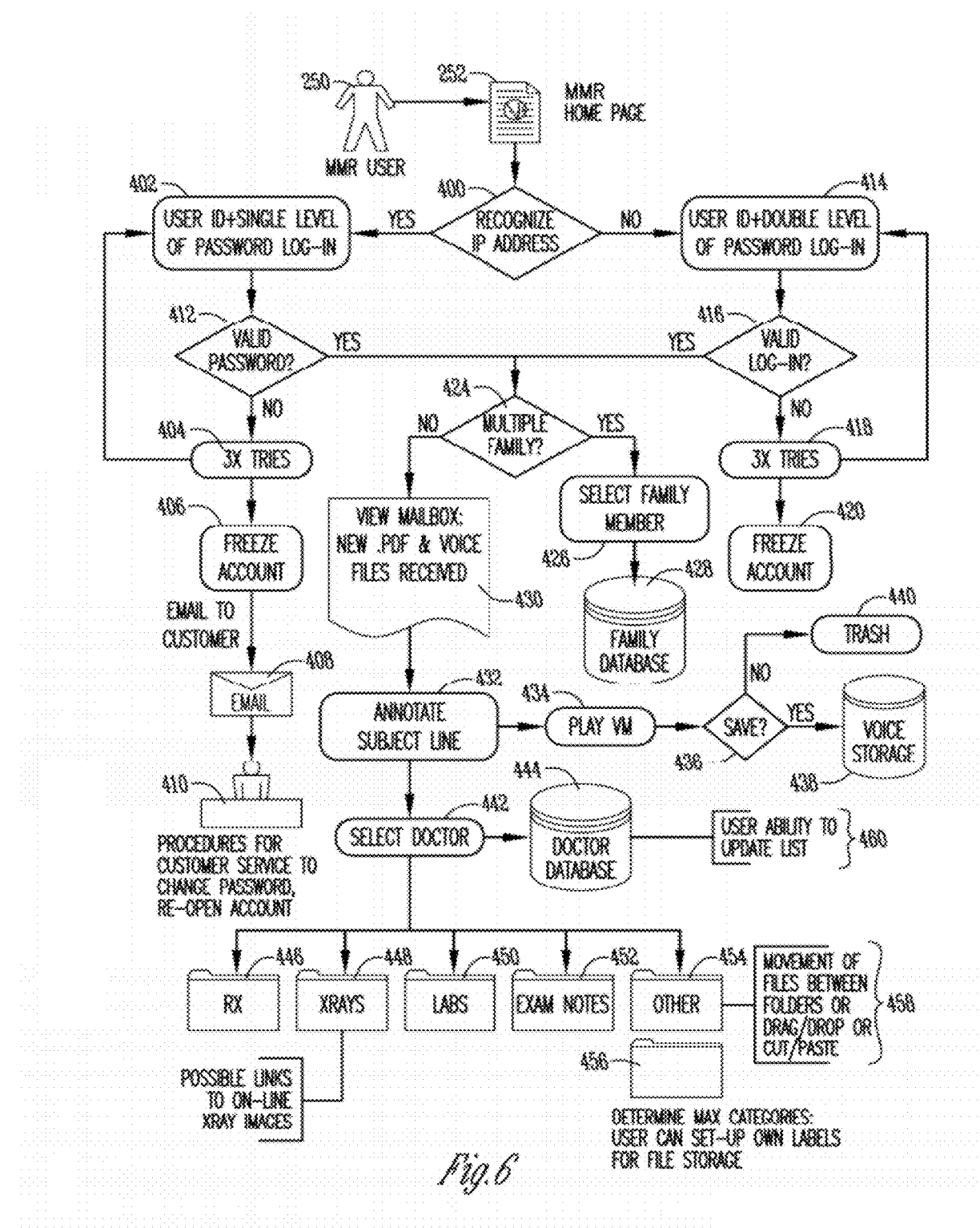
FIG. 6 is a flow diagram for accessing records according to one embodiment of the present invention.

The web site of the present invention provides a convenient location to collect and store healthcare records and provide secure access to the records. It also provides a convenient way to enroll in a service for providing online access to health records. FIGS. 5A and 5B provides one embodiment of an enrollment process In FIG. 5A, a user 250 accesses a home page 252 for a medical records web site. In step 254, a determination is made as to whether the user 250 is an existing member. If the member is, then in step 256 the user is provided access to their user interface as shown in FIG. 6. If not, then in step 258 a determination is made as to whether the user 250 agrees to terms and conditions of service. If not, then in step 260 the user is thanked for their interest but not allowed to continue. The user is also given the option or encouraged to output the terms and conditions to a printer in step 262 so that they can review them closely and maintain a copy for their records if they wish. If in step 258, the user agrees to the terms and conditions of service then in step 264 the system collects user data. User data 266 can include last name, first name, address information, city, state, zip code, phone number, email/pager/mobile device information, emergency contact name, emergency contact phone number, primary care physician phone number, insurance information, allergies and medications, and/or other information. If all fields are received in step 268, then in step 272 the system assigns a user name and password. It is to be understood that the user may also request a particular username and/or set their own password. Where a user selects their own password, then in step 270, a determination is made as to whether the password meets security requirements. For example, there may be a minimum number of characters required, or there must be at least one numeric character, or other requirements. Where the user is allowed to select their own name, in step 274, a username database is searched and in step 276 a determination is made as to whether or not the name is available. If it is, then in step 278 the user is permitted to create a personal identification number (PIN). In step 280, a rule such as one requiring a particular number of digits or a particular minimum digits is applied. In step 282 the PIN is validated and the enrollment process proceeds to billing options in step 284. In FIG. 5B, the user is allowed to choose a plan in step 286. The individual could, for example, choose an individual or family plan from the plan options 288. In step 290, the user enters credit card information 292 which may include a credit card number, billing address, and CW number. This information is then submitted to a payment processor 294. In step 298, a determination is made as to whether the credit card information can be authorized for payment. If not, then the number of retries is determined in step 296 and the user is allowed to re-enter their credit card information in step 290. If there have already been two tries to validate credit card information, then in step 300 the individual is told that they can not enroll at this time and should try again later. If payment is authorized in step 298 then in step 302 a dedicated toll free phone number is assigned and an IP address associated with the user is registered. In step 304 a user account is created. In step 306 an email notification confirming registration is sent to the user. In step 308 the user can begin to setup their personal web site such as their database of doctors, family members, calendar, and otherwise configure their web site.

Where a calendar is used, the present invention contemplates that the calendar can be synchronized with an application such as Microsoft Outlook, a calendar program associated with a PDA, or other personal information manager.

After registration, the user can access the user interface of the web site. FIG. 6 illustrates one embodiment of the user interface 256. The user 250 can access the homepage 252. In step 400, a determination is made as to whether the system recognizes the ip address being used by the user as being associated with the user. If the ip address is not recognized then extra security measures are taken beginning in step 414. In step 414 a username and a double level of password log-in is required. If a valid log-in, then the process proceeds to step 424. If not, then in step 418, the number of invalid log-in attempts or tries is monitored and if it is three, then in step 420 the account is frozen. Returning to step 400, if the ip address is recognized as being associated with the user, then in step 402 a username and a single level of password log-in is required. In step 412 a determination is made as to whether or not the password is valid. If a valid password, then the process proceeds to step 424. If not, then in step 404 a determination is made as to the number of invalid attempts. After three invalid attempts, in step 406 the account is frozen and in step 408 an email is sent to the individual who may, in step 410, implement procedures to change the password and re-open the account.

Returning to step 424, a determination is made as to whether the account is associated with an individual or a family. If the account is associated with a family, then in step 426, the user can select the family member and access the family database 428. If, in step 424 the account is not a family account, then in step 430 the user can view their mailbox showing new PDF files and voice files. Preferably, these new files include date and time stamps so that the user can see when the files were received.

In step 432, the user is allowed to annotate the messages to better identify the messages in a manner that is convenient for the user. In step 434, the user can play the voicemail messages. In step 436, the user can choose to save the messages to voice storage 438 or to send the message to the trash 440. In step 442, the user can select a doctor to associate with the voicemail messages. For example, the doctor from which the voicemail or imaged document was received. Preferably the doctor is within the doctor database 444. If not, then in step 460, the user can update the doctor database 444 to include the doctor. The user can then organize the voicemail or document according to the user's preference into one or more file folders. Examples of file folders include RX 446, XRAYS 448, LABS 450, EXAM NOTES 452, OTHER 454. The user can make new file folders such as file folder 456 and identify it appropriately. The user interface offers functions 458 such as movement of files between folders, drag and drop, cut and paste, and/or other functions that will assist the user in organizing their records.

The present invention provides for each of the file folders to be protected with one or more additional passwords. Such an implementation is particularly useful in a number of contexts. For example, the use of multiple passwords allows information such as insurance information, financial information, or other proprietary information to be protected differently than the medical records.

Another example of where this extra layer of security can be useful is where a single account is shared by a family consisting of two parents and multiple children. Each parent may have their own folder separately password protected so that the other parent can not access their folder, but still allowing both parents to access the folders for the children.

Figure 7:
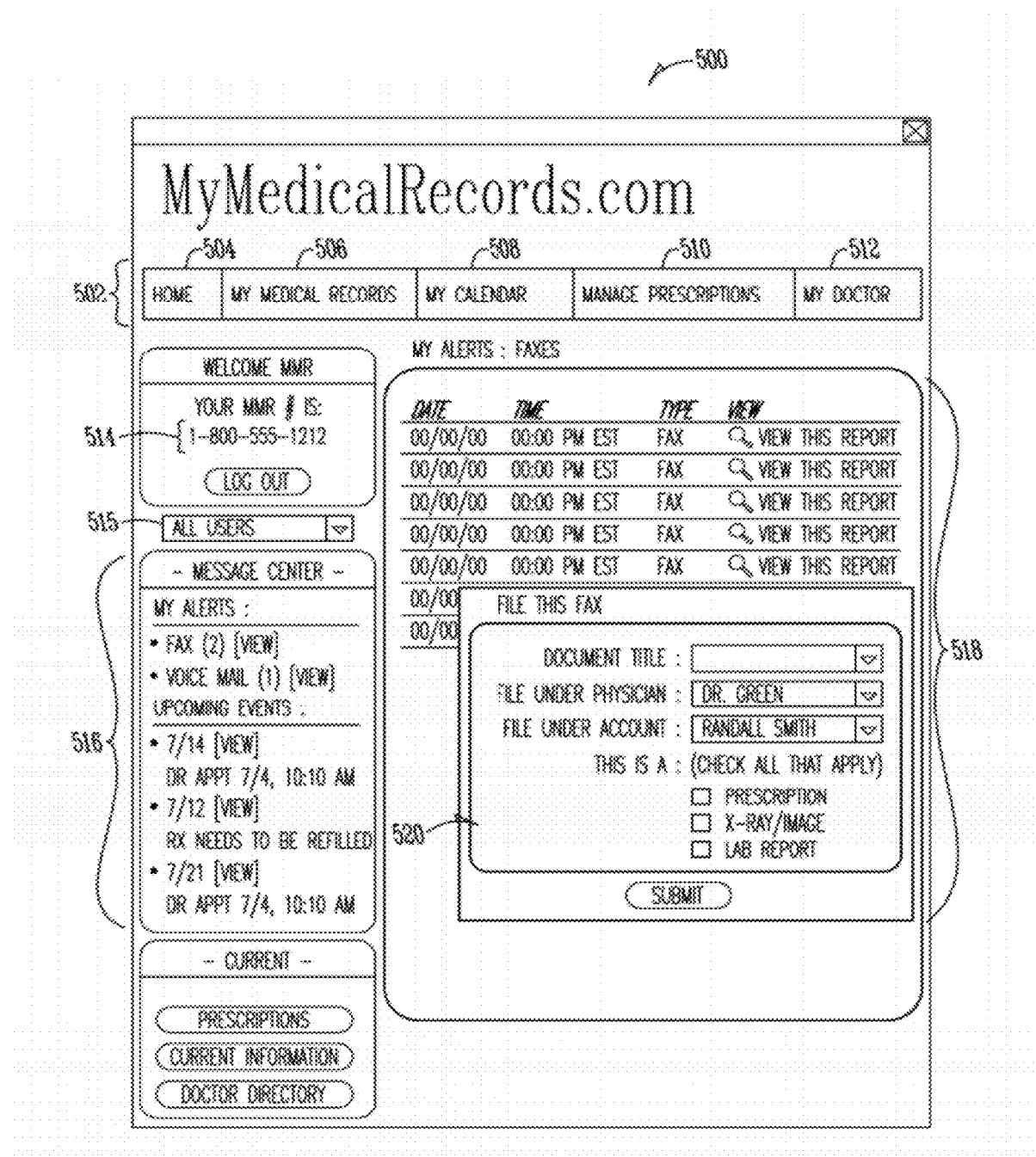
FIG. 7 is a screen display of a web site according to one embodiment of the present invention.

FIG. 7 illustrates one embodiment of a screen display of the present invention. In FIG. 7, the screen display 500 includes a menu bar 502 along the top with different menu items such as "Home" 504, "My Medical Records" 506, "My Calendar" 508, "Manage Prescriptions" 510 and "My Doctor" 512. The screen display 500 also includes a reminder to the individual of their LIFELINE toll free dedicated phone number 514. A message center 516 includes alerts as to recent faxes, voicemails, doctor appointments, prescription refills, or other related events. The user can view the recent faxes 518, and for each fax, can file it using fax filing options 520 which allow the user to give a document title to the fax, associate a physician with the fax, file the fax under a particular account where the account is a family account, and identify the fax as a prescription, x-ray/image, or lab report.

It should also be appreciated that a user need not fax themselves documents. Instead, the user can upload scanned documents or other files in any number of formats.

Figure 8:
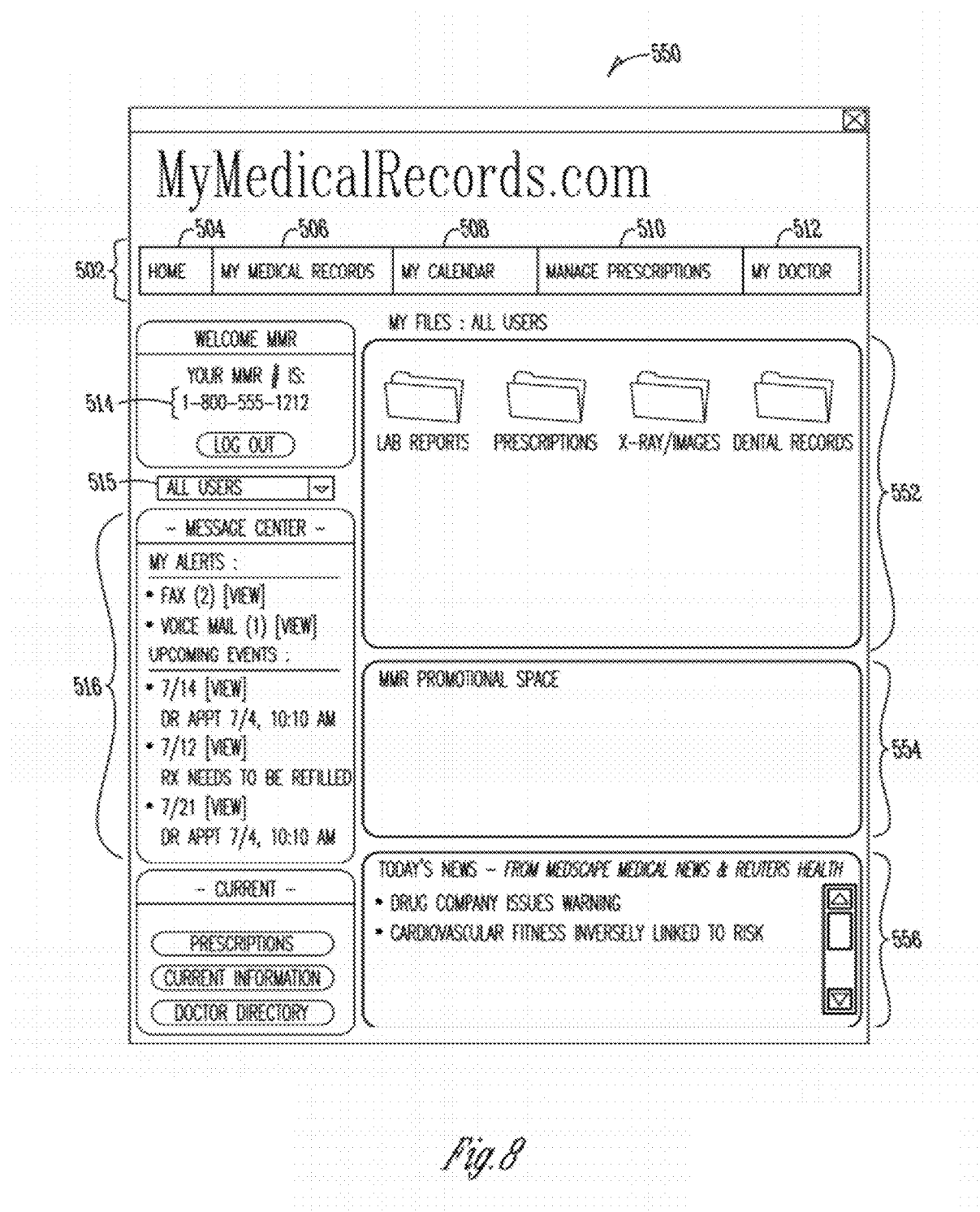
FIG. 8 is another screen display of a web site according to one embodiment of the present invention.

FIG. 8 illustrates another example of a screen display according to one embodiment of the present invention. In FIG. 8, the screen display 550 also includes a files section 552 wherein different folders are shown for storing and organizing information. This allows a user to store records in a manner appropriate for them. In one embodiment, the folders can include separate folders for lab reports, prescriptions, x-ray/images, dental records, lab reports, prescriptions, and all records. As shown in FIG. 8, there is a promotional space 554. The present invention allows for promotional material to be placed in the promotional space 554 that is of potential interest to the user. The promotional information can come from a third party source or advertiser. In additions, news information may be placed in a news information portion 556 of the web page. The news information can include breaking news regarding the medications that the patient is on, health and fitness news, or other news of potential interest or importance to the user.

Figure 9:
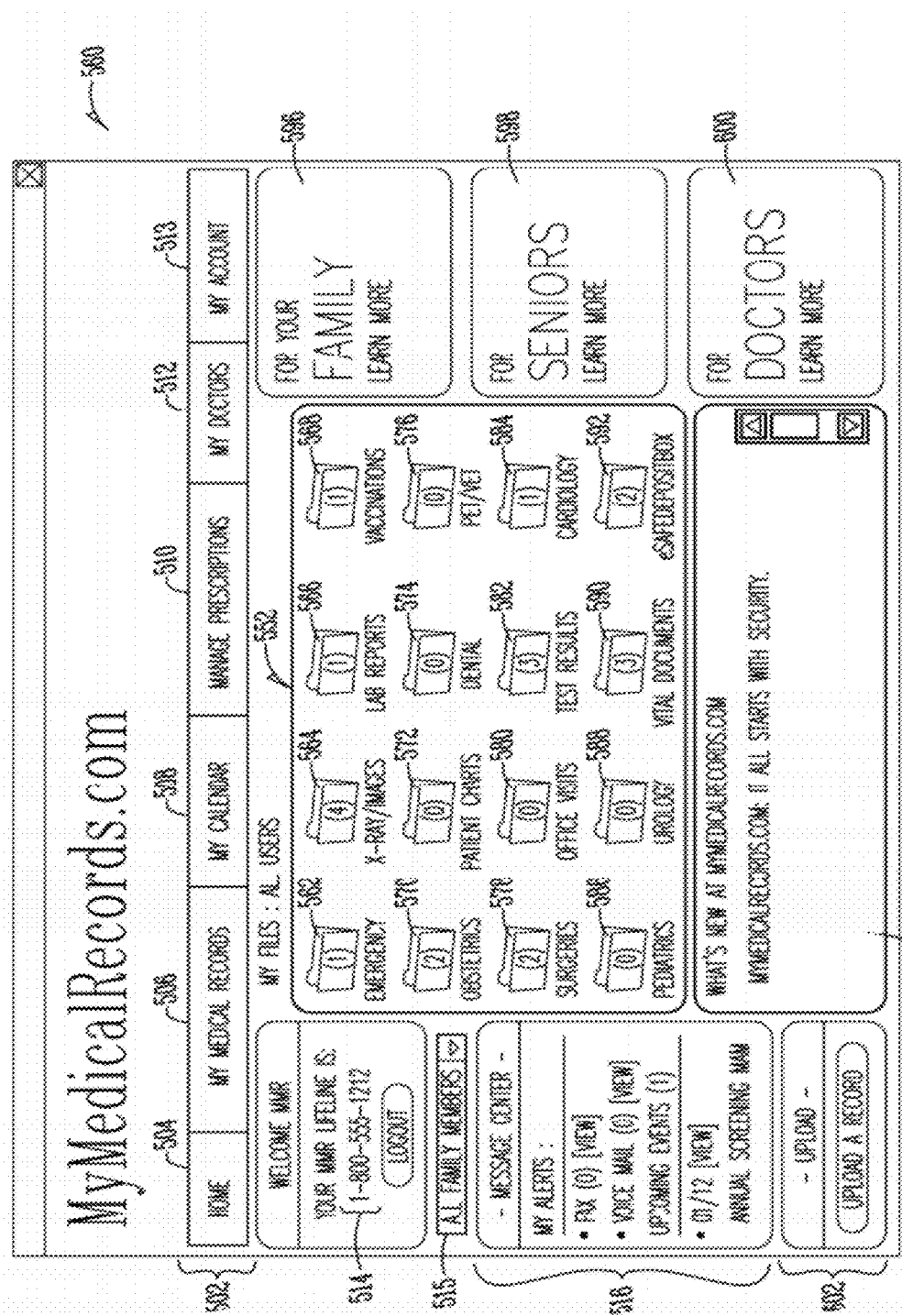
FIG. 9 is a screen display according to one embodiment.

FIG. 9 is another example of a screen display 560 according to one embodiment of the present invention. Note that a MYACCOUNT option 513 is shown near the top of the screen display 560. Also note that a user is allowed to select a family member using the dropdown list box 515. There is also an upload record option 602 provided so that a user may upload files of various types directly to their account.

Shown in the MY FILES portion 552 are a plurality of file folders, including: EMERGENCY folder 562, X-RAY/IMAGES folder 564, LAB REPORTS 566, VACCINATIONS 568, OBSTETRICS 570, PATIENT CHARTS 572, DENTAL 574, PET/VET 576, SURGERIES 578, OFFICE VISITS 580, TEST RESULTS 582, CARDIOLOGY 584, PEDIATRICS 586, UROLOGY 588, VITAL DOCUMENTS 590, eSAFEDEPOSITBOX 592. The various file folders shown provide a convenient method for users to organize their files. Note that each folder indicates how many files are stored within the file folder.

A WHAT'S NEW portion 594 allows users to learn about new features or other information. A FAMILY panel 596 can display information or links to information relevant to families. A SENIORS panel 598 can display information or links to information relevant to seniors. A DOCTORS panel 600 can display information or link to information relevant to doctors. Of course, the present invention contemplates that panels 596, 598 and 600 need not be present, and where present can be used to convey other types of information of potential interest to users.

Figure 10:
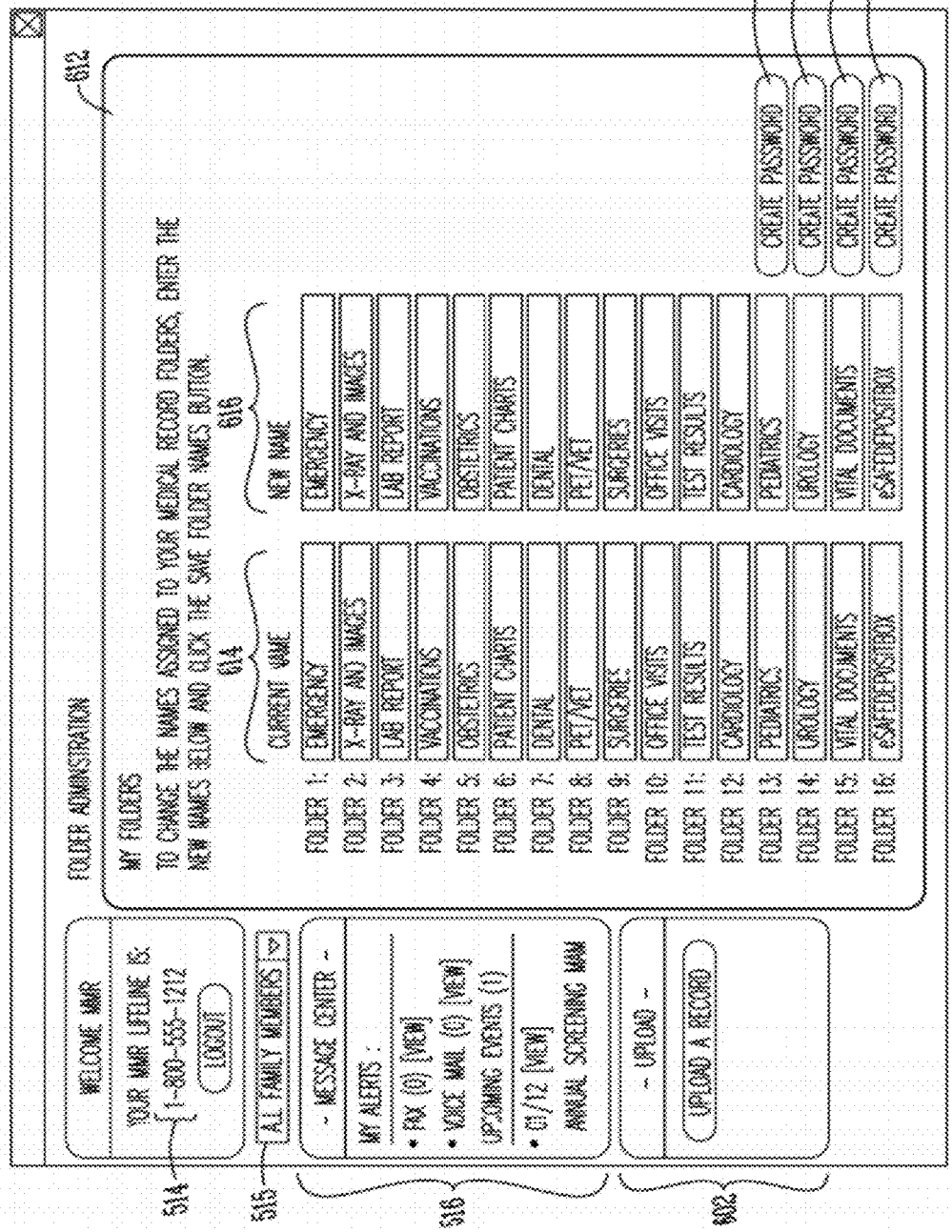
FIG. 10 is a screen display for folder administration according to another embodiment.

FIG. 10 is another example of a screen display according to one embodiment of the present invention. The screen display 610 allows for folder administration. A folder administration portion 612 includes a listing of multiple folders (16 shown) with a column 614 indicating the current name for each folder and a column 616 indicating the new name to be assigned to each folder. In operation a user can change the name of the folders to suit their particular needs. Note that at least a portion of the folders have a password associated with them. This provides an additional layer of security to these files.

Figure 11:
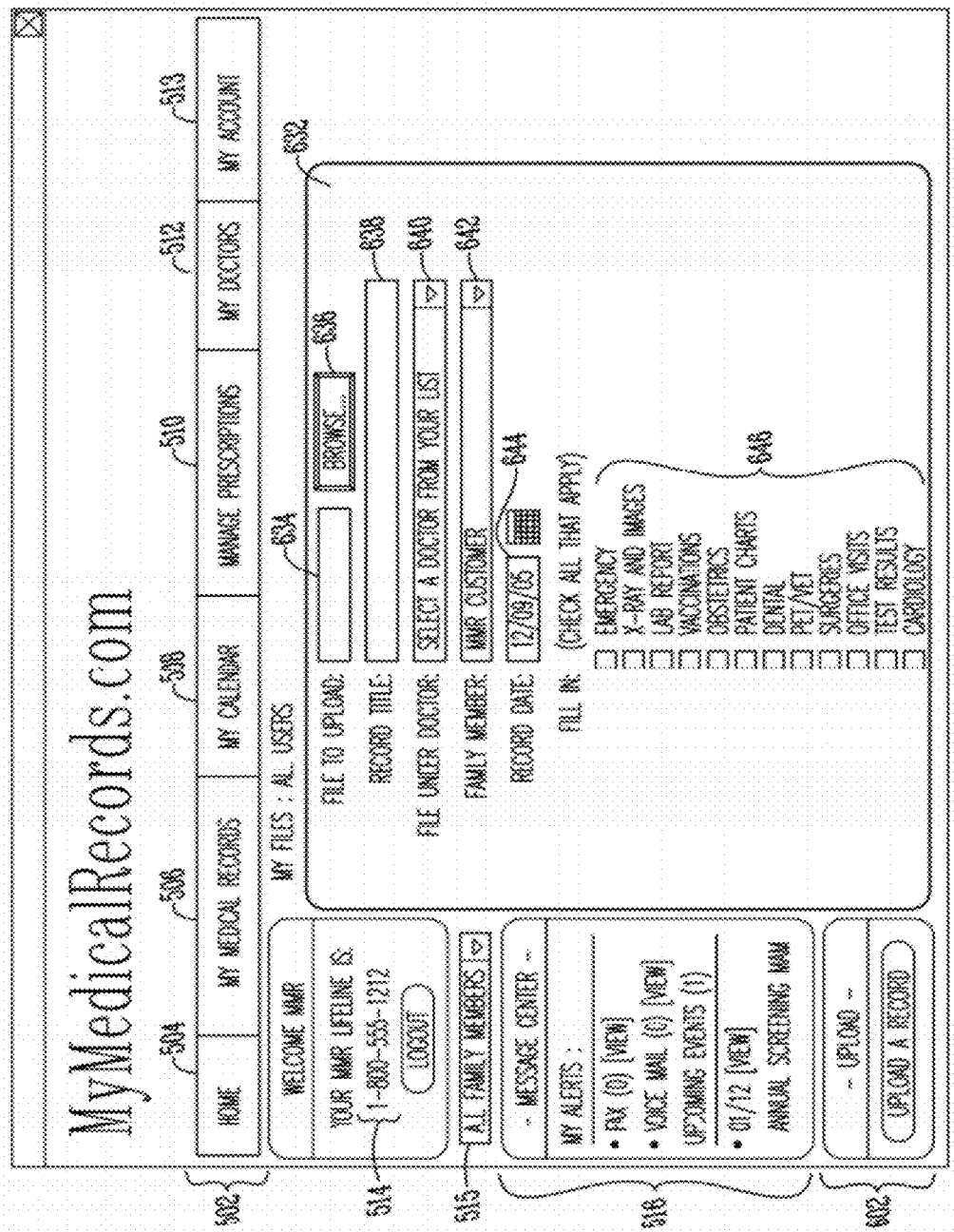
FIG. 11 is a screen display for an uploaded file feature according to another embodiment of the present invention.

FIG. 11 is a screen display for an uploaded file feature according to another embodiment of the present invention. The screen display 630 allows for uploading a medical record 602. The upload a record window 632 allows the user to select a file to be uploaded 634 by browsing 636 to the location of the stored file. For example, if the user has chest x-rays saved in a picture format such as a jpeg, they would be able to browse 636 to the file and upload the file 634 to add to or to make current their present set of medical records. The upload a record window 632 also allows the user to record a title 638 for the file uploaded 634. Additionally, the uploaded a record window 632 allows the user to associate the file uploaded 634 with the appropriate doctor selected from a drop-down list 640. If the account is family or joint type account and allows storing medical records for multiple persons, the user may use the drop-down menu 642 to select the family member 642 to whom this newly uploaded file 634 should be associated with. The upload a record window 632 also allows the user to record a date 644 associated with the newly uploaded file 634. Lastly, the user has the option of selecting the individual folders 646 where he or she would like a copy of the newly uploaded file 634 to be saved. For example, the user may wish to save the chest x-rays in the x-ray and images folder as well as other folders, such as the emergency folder, lab report and/or surgeries folder. The upload a record window 632 allows the user to periodically update their personal medical records with important medical information and associate that information with the appropriate folders. The upload a record window 632 also makes it easy for the user to browse to and save medical files in electronic form in a convenient and organized manner.

In one embodiment, not only is a password required to access the website, but an additional password is required to access such a folder. This feature can be advantageous in a number of different situations. For example, a family may share an account, but each spouse may maintain certain files in confidence from the other. Or where healthcare information is accessed in an emergency (or through fraudulent use of an emergency card), the most private information which is protected with a second level of password protection remains secure. As shown there are buttons 618, 622, 624, 626 for providing a secondary level of password protection.

FIG. 15 illustrates one embodiment of using the health-related information collected to provide additional benefits to a consumer. For example, the present invention allows for a system 800 that includes a personal health records database 850 and a drug interactions database 852 operatively connected to an analysis system 854. The analysis system 854 is operatively connected to a drug interaction reporting component 856. The personal health records 850 includes information regarding which prescription drugs are being taken by the user. The drug interactions database 852 includes information regarding known interactions between different drugs. The analysis system 854 analyzes the prescription drugs taken by the user to determine if there is any known interaction that may be adverse in any way to the user. Based on the results of this analysis, the drug interaction reporting component 856 reports the results to the user, their pharmacist, doctor, or other healthcare provider as appropriate. The present invention contemplates that drug interaction reporting 856 can be reported in different ways to different people based on factors such as user preferences regarding the drug interacting reporting, the severity or certainty of a determined adverse drug interaction, or otherwise. The present invention contemplates that in addition to drug interaction analysis and reporting, other types of analysis and reporting can be performed on the personal health records. One of the advantages of the present invention is that it allows for a convenient method to build and maintain complete and up-to-date health records, thus allowing the personal health records to be analyzed in any number of ways.

The present invention provides for numerous other features and advantages. For example, the web site can provide reminders for doctor appointments, prescription refills, or other events through email reminders or text messaging reminders. In addition, the web site allows the user to select the option of sending information via fax to a care provider. For example, a user can fax a prescription to their pharmacy of choice. In addition, the user can fax their medical records received from one healthcare provider to another healthcare provider.

According to another embodiment of the present invention, the healthcare records can include both medical records as well as dental records. In addition, the healthcare records can include, healthcare records not just for humans, but for pets as well. Thus, a family could manage healthcare records for every member of the family, including one or more pets.

According to another aspect of the present invention, other vital records are also stored on the web site. Examples of other types of vital records include wills, living wills, healthcare power of attorneys, and related information.

The present invention is not to be limited to the specific disclosure provide herein. The present invention contemplates numerous variations as may be appropriate in a particular context, environment, or situation.

What is claimed is:

1. A method for providing a use with the ability to access and collect personal health records associated with the user in a secure and private manner, the method comprising:
   associating access information with the user for the user to use to access a server storing files comprising personal health records associated with the user in a computer readable storage medium;
   providing the user with a user interface on a computing device to remotely access the personal health records stored on the server, the user interface providing for organizing the files into separate file folders with functionality for the user to name the file folders and add file folders and individually assign password protection to each of the file folders;
   receiving at the server the files comprising personal health records associated with the user from a health care provider associated with the user;
   receiving at the server a request from the user made through the user interlace of the computing device for access to the files, wherein the access information is associated with the request;
   sending the user a file containing the personal health records associated with the user from the server to the computing device in response to the request;
   wherein the files are maintained on the server independently from any files maintained by the health care provider and wherein the files are managed privately by the use independently from the health care provider.

2. The method of claim 1 wherein the access information comprises a password.

3. The method of claim 1 further comprising receiving at the server additional files comprising personal health records associated with the user from a second health care provider associated with the user.

4. The method of claim 3 wherein the files comprise image file format files.

5. The method of claim 4 wherein the image file format files include image representations of medical records, living wills, power of attorneys, or other medical or legal documents.

6. The method of claim 3 wherein the files comprises audio recordings.

7. The method of claim 6 wherein the audio recordings include voicemail recordings from a health care provider.

8. A method for providing a user with the ability to access and collect personal health records associated with the user in a secure and private manner, the method comprising:

associating access information with the user for the user to use to access a server storing files comprising personal health records associated with the user in a computer readable storage medium;

providing the user with a user interface on a computing device to remotely access the personal health records stored on the server;

receiving at the server the files comprising the personal health records associated with the user from a health care provider associated with the user;

receiving at the server a request from the user made through the user interface of the computing device for access to the files, wherein the access information is associated with the request;

sending the user a file containing the personal health records associated with user from the server to the computing device in response to the request;

wherein the files are maintained on the server independently from any files maintained by the health care provider and wherein the files are managed privately by the user independently from the health care provider.

9. The method of claim 8 wherein the access information comprises a password.

10. The method of claim 8 further comprising further comprising receiving at the server additional files comprising personal health records associated with the user from a second health care provider associated with the user.

11. The method of claim 10 wherein the files comprise image file format files.

12. The method of claim 11 wherein the image file format files include image representations of at medical records, living wills, power of attorneys, or other medical or legal documents.

13. The method of claim 10 wherein the files comprises audio recordings.

14. The method of claim 13 wherein the audio recordings include voicemail recordings from a health care provider.

15. A method for providing a user with the ability to access and collect personal health records associated with the user in a secure and private manner, the method comprising:

associating access information with the user for the user to use to access a server storing files comprising personal health records associated with the user in a computer readable storage medium;

providing the user with a user interface on a computing device to remotely access the personal health records stored on the server, the user interface providing for organizing the files into separate file folders with functionality for the user to name the file folders and add file folders and individually assign password protection to each of the file folders;

receiving at the server the files comprising records associated with the user from a health care provider associated with the user;

receiving at the server a request from the user made through the user interface of the computing device for access to the files, wherein the access information is associated with the request;

sending the user a file containing the personal health records associated with the user from the server to the computing device in response to the request;

receiving at the server a request from the user made through the user interface of the computing device for sending one of the files to a second health care service provider;

sending the second health care service provider the one of the files from the server;

wherein the files are maintained on the server independently from any files maintained by the health care provider and wherein the files are managed privately by the user and independently from the health care provider and wherein the user interface is not provided to the health care provider.

* * * * *

UNITED STATES PATENT AND TRADEMARK OFFICE
CERTIFICATE OF CORRECTION

| | | Page 1 of 1 |
|---|---|---|
| PATENT NO. | : 8,301,466 B2 | |
| APPLICATION NO. | : 13/041809 | |
| DATED | : October 30, 2012 | |
| INVENTOR(S) | : Lorsch | |

It is certified that error appears in the above-identified patent and that said Letters Patent is hereby corrected as shown below:

Col. 16, Claim 1, Line 21:
DELETE after a "use"
ADD after a --user--

Col. 16, Claim 1, Line 48:
DELETE before independently "use"
ADD before independently --user--

Signed and Sealed this
Twenty-ninth Day of January, 2013

David J. Kappos
*Director of the United States Patent and Trademark Office*